US00PP11222P

United States Patent [19]

Zary

[11] Patent Number: Plant 11,222

[45] Date of Patent: Feb. 15, 2000

[54] HYBRID TEA ROSE PLANT NAMED 'JACHOV'

[75] Inventor: Keith W. Zary, Thousand Oaks, Calif.

[73] Assignee: Bear Creek Gardens, Inc., Medford, Oreg.

[21] Appl. No.: 09/001,935

[22] Filed: Dec. 31, 1997

[51] Int. Cl.[7] ..... A01H 5/00

[52] U.S. Cl. ..... Plt./130

[58] Field of Search ..... Plt./130, 131, 132

*Primary Examiner*—Howard J. Locker

*Attorney, Agent, or Firm*—Klarquist Sparkman Campbell & Leigh & Whinston, LLP

[57] ABSTRACT

A hybrid tea rose plant having bicolor flowers that are pink on the upper side and yellow on the reverse; a vigorous, upright growth habit; hybrid tea flower form; and moderate fragrance.

1 Drawing Sheet

The present invention relates to a new and distinct variety of rose plant of the hybrid tea class which was originated by me by crossing the variety 'JAColite,' U.S. Plant Pat. No. 4,167, with the variety 'JACtwin,' U.S. Plant Pat. No. 4,437.

The primary objective of this breeding was to produce a new rose variety having the vigorous, upright growth, large flowers, and good flower form of the female parent combined with the bicolor flower effect of the male parent. The objective was substantially achieved, along with other desirable improvements, as evidenced by the following unique combination of characteristics that are outstanding in the new variety and that distinguish it from its parents, as well as from all other varieties of which I am aware:

1. Flower color that is pink with a light yellow reverse;
2. Vigorous upright plant habit;
3. Good hybrid tea flower form;
4. Moderate fragrance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—JAColite (U.S. Plant Pat. No. 4,167).

*Pollen parent*.—JACtwin (U.S. Plant Pat. No. 4,437).

Classification:

*Botanical*.—Rosa hybrida.

*Commercial*.—Hybrid tea.

FLOWER

Observations made from specimens grown in a garden environment at Somis, Calif. from March–October 1996.

Blooming habit: Recurrent.

Bud:

*Size*.—Two inches long when the petals start to unfurl.

*Form*.—The bud form is long, pointed ovoid.

*Color*.—When sepals first divide, bud color is Yellow Orange Group 14D and Red Group 54C. When half blown, the upper sides of the petals are Red Group 54C; and the lower sides of the petals are Yellow Orange Group 14D.

*Sepals*.—Color: Green group 138C with a reddish cast when exposed to sunlight. Surface texture: Covered with fine hairs. There are three normally to heavily appendaged sepals. There are two unappendaged sepals with hairy edges.

*Receptacle*.—Color: Green Group 137C. Shape: Apple. Size: Medium (⅝" long×¼" wide). Surface: Smooth.

*Peduncle*.—Length: Short (2" to 2½"). Surface: Smooth with occasional glands. Color: Medium green and bronzy. Strength: Stiff, erect.

Bloom:

*Size*.—Large. Average open size is 4–4½ inches.

*Borne*.—Singly.

*Stems*.—Medium, (16–20").

*Form*.—When first open: High centered. Permanence: Retains its form to the end; outer petal edges curl back.

*Petalage*.—Number of petals under normal conditions: 30.

*Color*.—The upper sides of the petals are Red Group 54C. The reverse sides of the petals are Yellow Orange Group 14D. The base of each petal has a small (¼"×¼") deep yellow (Yellow Orange Group 14B) half moon at the point of attachment. The major color on the upper side is Red Group 54C for the upper two-thirds of the petal, then Yellow Group 14C with Yellow Group 14B at the point of attachment.

*Variegations*.—There are whitish streaks on the guard petals. Also, veins are darker on all petals.

*Discoloration*.—At the end of the first day: No change. At the end of the third day: No change. By day four or five there is a fading of the pink upper surface in bright sunshine to Red Group 54D.

*Fragrance*.—Moderate.

Petals:

*Texture*.—Thick.

*Shape*.—Round.

*Form*.—Tips slightly recurved, edges slightly quilled.

*Arrangement*.—Imbricated. Petaloids in the center are few.

*Persistence*.—Drop off cleanly.

*Lastingness*.—On the plant: Long (seven days). As a cut flower: Long (nine to ten days).

Reproductive parts:

*Anthers*.—Size: Medium. Quantity: Many. Color: Yellow. Arrangement: Regular around styles.

*Filaments*.—Color: Yellow.

*Pollen*.—Color: Gold yellow.

*Styles*.—Color: Cream.

*Stigmas*.—Color: Greenish-white.

Plant:

*Form*.—Bush.

*Growth*.—Vigorous; upright; branching; Height unpruned, outside after one full growing season in Southern California will be six feet; width four feet.

*Foliage*.—Number of leaflets on normal mid-stem leaves: Five.

*Size*.—Large.

*Quantity*.—Abundant.

*Color*.—New foliage: Upper and lower surfaces: Greyed-Red Group 178B. Old foliage: Upper surface: Green Group 139A. Lower surface: Green Group 139C.

*Shape*.—Pointed oval.

*Texture*.—Upper side: Leathery, glossy.

*Edge*.—Serrated.

*Serration*.—Single, small.

*Petiole rachis*.—Color: Reddish.

*Petiole underside*.—Smooth with occasional prickles.

*Stipules*.—Medium (½"); serrated, bearded.

*Disease resistance*.—Resistant to mildew and rust under normal growing conditions at Somis, Calif.

Wood:

*New wood*.—Color: Reddish. Bark: Smooth.

*Old wood*.—Color: Green. Bark: Smooth.

Prickles:

*Quantity*.—On main canes from base: Ordinary. On laterals from main canes: Ordinary.

*Form*.—Medium (¼"); hooked downward.

*Color when young*.—Red.

Small prickles:

*Quantity*.—On main stalks: None. On laterals: None.

I claim:

1. A new and distinct variety of rose plant of the hybrid tea class, substantially as herein shown and described, characterized particularly as to novelty by novel bicolor flowers that are pink on the upper side and yellow on the reverse, vigorous upright growth habit, hybrid tea flower form, and moderate fragrance.

* * * * *

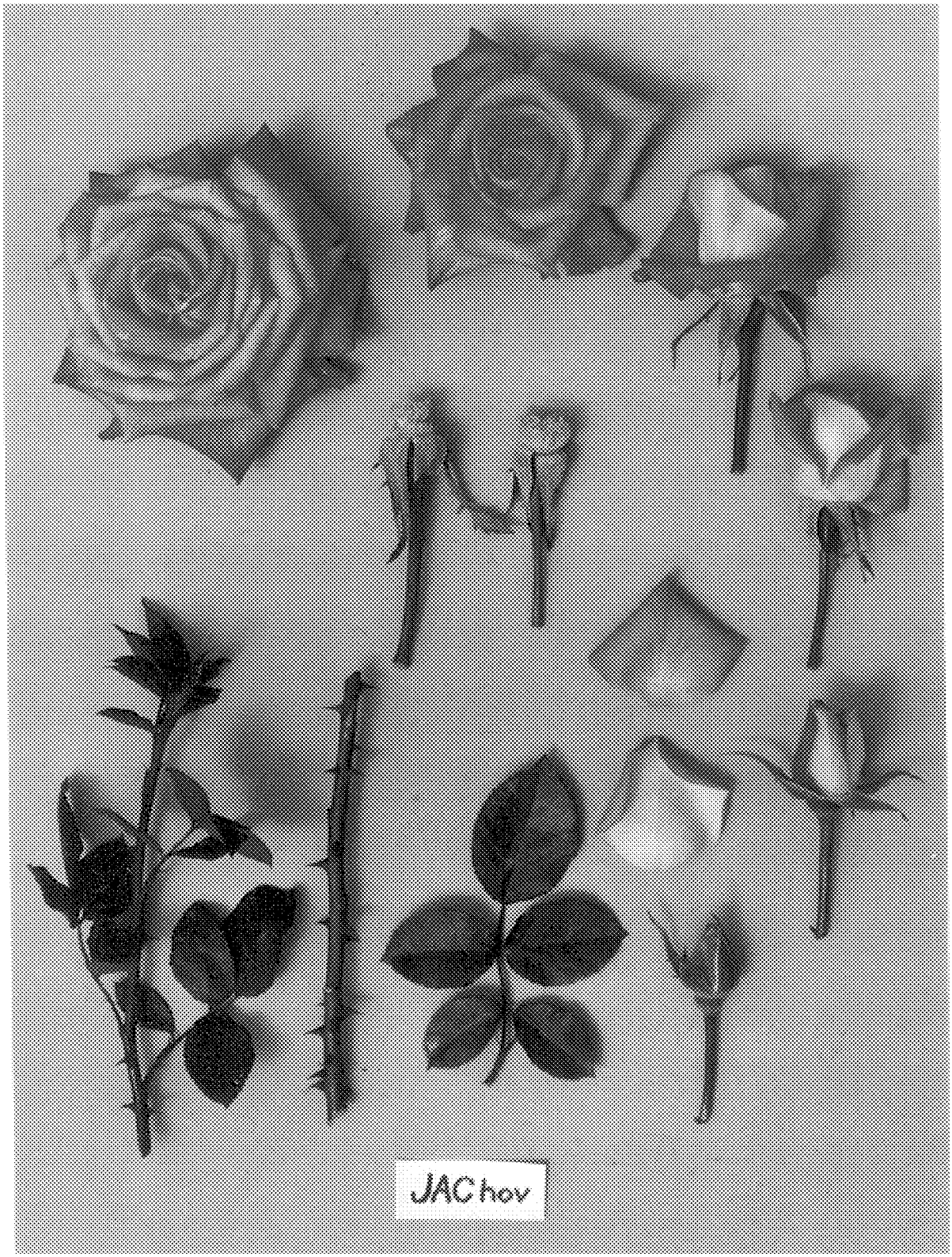
JAChov